United States Patent
Scivoletto et al.

(10) Patent No.: US 10,376,548 B2
(45) Date of Patent: Aug. 13, 2019

(54) ANIMAL HEALTH IMPROVEMENT COMPOSITION AND METHOD

(71) Applicant: ABSORBezz LLC, Fort Lauderdale, FL (US)

(72) Inventors: Joseph Scivoletto, Margate, FL (US); Steven Adelstein, Coral Springs, FL (US)

(73) Assignee: ABSORBEZZ, LLC, Fort Lauderdale, FL (US)

( * ) Notice: Subject to any disclaimer, the term of this patent is extended or adjusted under 35 U.S.C. 154(b) by 0 days.

(21) Appl. No.: 14/513,785

(22) Filed: Oct. 14, 2014

(65) Prior Publication Data

US 2015/0104424 A1    Apr. 16, 2015

Related U.S. Application Data

(60) Provisional application No. 61/889,618, filed on Oct. 11, 2013.

(51) Int. Cl.

| | |
|---|---|
| *A61K 35/741* | (2015.01) |
| *A23K 20/24* | (2016.01) |
| *A23K 50/10* | (2016.01) |
| *A23K 50/75* | (2016.01) |
| *A61K 36/22* | (2006.01) |
| *A23K 20/147* | (2016.01) |
| *A61K 31/198* | (2006.01) |

(52) U.S. Cl.
CPC .......... *A61K 35/741* (2013.01); *A23K 20/147* (2016.05); *A23K 20/24* (2016.05); *A23K 50/10* (2016.05); *A23K 50/75* (2016.05); *A61K 31/198* (2013.01); *A61K 36/22* (2013.01)

(58) Field of Classification Search
CPC combination set(s) only.
See application file for complete search history.

(56) References Cited

U.S. PATENT DOCUMENTS

| | | | |
|---|---|---|---|
| 2006/0094658 A1 | 5/2006 | Currie et al. | |
| 2008/0038370 A1 | 2/2008 | Holt | |
| 2008/0241273 A1 | 10/2008 | Scivoletto | |
| 2011/0232173 A1 | 9/2011 | Lefebvre | |
| 2012/0003175 A1* | 1/2012 | Hazan ................... | A61K 36/22 424/78.08 |

OTHER PUBLICATIONS

Pasioonline.com, Mastic Gum, Accessed Aug. 19, 2017, Available Online at: pasioonline.com/mastic-gum-500mg-capsules-pistacia-lentiscus-jarrow-formulas-en/.*
ELgubbi et al., Phytochemical, Mineral Compounds and Anti-Oxidation Studies on Pistacia Lentiscus Shoot Extract, Global Journal of Medical Research, vol. 14, No. 5-B Oct. 2014.*
Ain-Lhout et al., Comparison of proline accumulation in two Mediterranean shrubs subjected to natural and experimental water deficit, Plant and Soil, (2001) 230: pp. 175-183.*
Rockwell Nutrition, Gastric Repair Complex Capsules by Biogenesis Nutraceuticals, Available at least as early as Nov. 25, 2012, per review by "sammi"; Available online at: www.rockwellnutrition.com/Gastric-Repair-Complex-by-Biogenesis-Nutraceuticals.html #tablist.*
Surjushe et al., Aloe Vera: A Short Review, Indian Journal of Dermatology, 2008, 53(4): pp. 163-166.*
Baldwin, Aloe Vera, Dr. Christopher's Herbal Legacy, Accessed Jun. 15, 2018, Available Online at: www.herballegacy.com/Baldwin_Chemical.html.*
SelfNutritionData, Foods highest in Lysine and lowest in Arginine, Accessed Jun. 15, 2018, Available Online at: nutritiondata.self.com/foods-016083000000089000000-4.html.*
Tong et al., Meta-analysis: the effect of supplementation with probiotics on eradication rates and adverse events during *Helicobacter pylori* eradication therapy; Alimentary Pharmacology & Therapeutics, 25 (2007) pp. 155-168.*
International Search Report dated Feb. 10, 2015; Application Serial No. PCT/US2014/060479 in the name of Absorbezz, LLC.

* cited by examiner

*Primary Examiner* — Jennifer M. H. Tichy
(74) *Attorney, Agent, or Firm* — Johnson & Martin, P.A.; James David Johnson

(57) ABSTRACT

Compositions and methods are provided for improving the health of an animal by reducing certain diseases and by binding certain heavy metals that may be unintentionally introduced into the body of the animal from the environment. Compositions and methods are also provided for improving the feed conversion ratio of an animal. In addition, compositions and methods are provided for reducing nitrate pollution in the environment. In one embodiment, the composition may include mastic gum, a mixture of ionic minerals, and optionally an essential amino acid not produced by the animal. The ionic minerals may be derived from water sourced from an inland sea such as the Great Salt Lake, the Dead Sea, or another inland sea. The essential amino acid may be included in the form of a protein. The animal may be a ruminant, poultry, or other animal. Methods are also provided for processing mastic gum.

4 Claims, No Drawings

ANIMAL HEALTH IMPROVEMENT COMPOSITION AND METHOD

CROSS-REFERENCE TO RELATED APPLICATIONS

This application is a nonprovisional application of and claims priority from U.S. provisional patent application Ser. No. 61/889,618 filed on Oct. 11, 2013. The foregoing application is incorporated in its entirety herein by reference.

FIELD OF THE INVENTION

The present invention relates to a health improvement composition for mammals and related methods for preparing and using the composition. More particularly, the present invention relates to an animal health improvement composition that can be provided to ruminants and poultry. The invention also relates to methods for processing mastic gum, for improving a feed conversion ratio of an animal, and for reducing nitrate pollution in the environment.

BACKGROUND

Animals, including ruminants and poultry, are important sources of human food, consumer products (e.g., leather and feathers), and in some cases, work power. Ruminants are mammals that digest plant-based food by chewing food multiple times. Ruminants acquire nutrients by a process where food is initially chewed, swallowed, partially softened, regurgitated, chewed again, and then digested. Ruminants include cattle, goats, sheep, giraffes, yaks, deer, camels, llamas, antelope, and other related animals. Poultry are domesticated birds kept to produce eggs, meat, and sometimes feathers.

For the agricultural industry and farmers, body mass for such livestock and poultry is important. The body mass of any given animal is affected both by digestive absorption and metabolic uptake of nutrients as well as disease conditions from which such animals may suffer. Animals may also suffer from poor nutrition due to the presence of heavy metals in their bodies.

Coccidiosis is a condition caused by parasitic organisms of the *Eimeria* species of microorganisms. Coccidiosis can be a costly problem in livestock and poultry in that in early infestations the damage to the epithelial cells on the walls of the small intestine reduces the absorption of nutrients. Later, heavy infestations can result in permanent damage to the lining of the small intestine, anemia from blood loss from the damaged lining, and death if the infestation is severe enough.

In livestock, poultry, and other animals, ingestion of heavy metals present in the environment (e.g., in grazing pastures or water sources) can cause negative health effects both for the animal and for consumers who may ingest such animals. Heavy metals include aluminum, nickel, copper, iron, cadmium, arsenic, mercury, selenium, lead, and other heavy metals. The presence of heavy metals in an animal may affect uptake of nutritional minerals by the animal's body.

For example, selenium is a necessary, yet potentially dangerous, mineral for livestock. Selenium can increase lactation and health. Selenium typically has a narrow tolerance between deficiency and toxicity. When added to a composition, careful regulation may be important to control the quantity of the selenium in a composition.

Selenium may be found naturally by ruminants and other animals through foraging or other measures. Some areas of the U.S. and throughout the world are selenium deficient. For example, most of the northeastern and northwestern states have significant selenium deficiencies and supplementation may become necessary. Additionally, in some areas, such as the western states, soil selenium levels are sufficiently high that producers occasionally see symptoms of selenium toxicity in livestock.

Generally, dairy farmers, ranchers and keepers of ruminants and other animals are unaware of the level of selenium on their land and in the feed consumed by their livestock. However, improper amounts of selenium at a location may become apparent. For example, experiences with livestock eating either too much or too little selenium may produce livestock losses from either resulting condition.

Modern dairy cows are expected to produce tremendous amounts of milk to meet the demands of the world's growing population. High milk yield is only possible when good management is matched with good genetics. Formulating a ration to meet the needs of the cows in the herd depends on knowledge of many factors including body size, stage of lactation, level of production, and stage of gestation. This process may be made more complicated when the cow's appetite or capacity for feed intake is below the level that is needed to maintain her body, produce milk, and grow. Energy intake is usually less than energy requirements. In this stage, cows can experience a negative energy balance, meaning that the cow must use her body's stored nutrients to meet her milk production requirements. Cows in this stage of lactation typically lose weight and deteriorate in body condition.

If a cow calves without sufficient body reserves or body condition to make up for this negative energy balance, milk production may suffer. On the other hand, care may need to be taken to ensure a cow does not become overweight before she calves. The ideal feeding program may allow feeding each cow individually according to its specific needs. However, individualized feeding regimens may be difficult or impossible due to the difficulty in monitoring day-to-day changes in nutrient requirements for each cow and may be impractical from a labor and cost perspective due to the expense and manpower required to feed each cow individually. Instead, many farmers group feed cows according to their stage of lactation and level of milk production. While grouping strategies vary depending on herd size and the available facilities, three groups of lactating cows and two groups of dry cows is one common illustrative grouping strategy.

Early lactation of ruminants, such as cows, will now be discussed. The composition may facilitate early lactation in cows in a first period, before peak lactation. Ruminants, such as cows, can experience negative impacts on lactation during this period due to a negative energy balance. This period from calving to peak lactation is the most critical stage of lactation for a dairy cow. Every additional pound of peak milk production may result in about a 100 pound increase in milk production over an entire lactation, without limitation.

Mammals including ruminants need glucose for the synthesis of milk. In addition to secreting bile, the liver plays an important role in converting certain absorbed nutrients into compounds that are more useful to the animal. One example is the conversion of propionate and lactate absorbed from a rumen into glucose. The ruminant, such as a cow, needs glucose for the synthesis of milk. A ruminant also needs glucose for use by its brain and central nervous system, but often does not absorb a sufficient amount of glucose necessary for health plus milk production. The liver synthesizes nearly all of the glucose needed by the cow every day through gluconeogenesis. The liver may also convert absorbed fatty acids into forms better suited for transport through blood and use by the tissues, and may convert absorbed ammonia into the less toxic compound urea. Liver protective effects are associated with mastic gum ingestion. Mastic gum taken daily decreases levels of certain liver enzymes compared to initial levels, which is an indicator of better liver health.

Nutrient absorption will now be discussed in greater detail. Absorption of minerals primarily occurs within the small intestines. As food matter passes through the intestines, minerals transfer into the blood stream through the walls of the intestines by way of the villi. Often, these minerals are in an ionic form. Although stomach acid helps to ionize the minerals in foods, a mineral supplement can contain naturally ionized minerals that can be fully or nearly fully absorbed by the animal. Certain trace minerals may exist in relationship to one another so that, for example, excess amounts of one trace mineral can lead to imbalances in others. Optimal absorption of most trace minerals occurs when such minerals pass into the intestine in ionic form.

Calcium is another essential nutrient, being required for proper contraction of muscles in livestock. Severe hypocalcaemia prevents skeletal muscle contractions so that, if left untreated, the clinical syndrome known as milk fever may occur. Muscle contraction may be reduced by a decrease in blood calcium. Contraction rate and strength of the smooth muscle of the intestinal tract of a ruminant may be directly proportional to blood calcium concentration.

Milk fever is generally associated with the day of calving but many cows may remain with subclinical hypocalcaemia for about the first week of lactation. For proper muscle contraction and relaxation to occur, magnesium and calcium should be present in proper amounts in the body, which can be difficult to achieve even on a standard healthy diet for livestock. Intracellular calcium concentration also plays a role in the function of immune cell receptors.

The essential oil of mastic gum (*Pistacia* lentiscus var. chia) has been shown to exhibit anti-microbial properties on gram positive and gram negative bacteria in broth and in model food systems. The addition of mastic gum in broth culture inoculated with *Staphylococcus aureus, Lactobacillus plantarum, Pseudomonas fragi*, and *Salmonella enteritidis* may inhibit the growth of these organisms. The rate of inhibition may be greater on gram positive bacteria than on gram negative bacteria. In most cases, the size of inoculum and the concentration of mastic gum affect the growth/survival of the organisms.

Proper and efficient digestion and metabolization of protein is important to the health of animals, including ruminants and poultry. Proteins are composed of amino acids, which contain carbon, hydrogen, oxygen, and nitrogen. Some amino acids also contain sulfur in addition to the foregoing elements. Twenty-two amino acids are known to exist in nature. Amino acids bonded together in different combinations form the various types of proteins.

Proteins have many different functions in the body. They are important structural components of many tissues, and can be found in muscle, skin, feathers, hair, bone, fingernails, muscle tissues, other tissues, and blood. Several hormones are proteins, including insulin and bovine somatotropin. The enzymes important in digestion, absorption, and metabolism are all proteins.

Enzymes secreted by the abomasum, pancreas and small intestine can break the bonds between amino acids to separate the amino acids and allow them to be absorbed by an animal's body. Proteins typically must be broken down into their component amino acids before absorption. Amino acids can be divided into two groups: essential and nonessential. Essential amino acids are not produced by the body, and therefore, must be obtained through the animal's diet. Nonessential amino acids are produced by cells and do not need to be present in the animal's diet.

The essential amino acids include phenylalanine, histidine, isoleucine, leucine, lysine, methionine, tryptophan, valine, arginine, and threonine. In dairy rations, lysine and methionine are the most common limiting amino acids, because common feeds (e.g., corn, corn silage, and soybean meal) are relatively low in these amino acids compared to the quantities needed for milk synthesis. Fish meal and blood meal are good sources of lysine, while corn gluten meal, fish meal, and sunflower meal are good sources of methionine. Creating feed rations using small amounts of these protein supplements in addition to standard ingredients may increase milk protein yield and reduce nitrogen excretion in urine. The higher the productivity of an animal, typically the greater need for undegradable protein versus degradable protein. More common feed ingredients include proteins that are generally more degradable.

What is needed is a composition meeting nutritional requirements of an animal, such as a ruminant or poultry. What is needed is lower feed costs for the nutrients provided to an animal. What is needed is a composition to facilitate increased reproductive performance of an animal, such as a ruminant or poultry. What is needed is a composition to improve egg production from an animal. What is needed is a composition to facilitate increased milk protein yield by a lactating animal, such as a ruminant. What is needed is a composition to minimize nitrogen excretion from an animal. What is needed is a composition to induce early lactation for an animal, such as a ruminant.

SUMMARY

The present invention advantageously may provide a composition and compositions nearly or precisely meeting nutritional requirements of an animal, such as a ruminant or a poultry bird. In addition to ruminants and other mammals, the composition may also be fed to or mixed with the feed given to other types of animals including, but not limited to, birds and poultry (e.g., chickens, turkeys, ducks, geese, other waterfowl, ostriches, pigeons, etc.) and reptiles (e.g., alligators and crocodiles), and other animals that are farm-raised. The composition can include mastic gum, a source of calcium, and a source of magnesium all of which are dissolved in water containing dissolved ionic trace minerals. Ingestion of the composition by an animal improves the animal's digestion, liver function, milk production (in the case of ruminants), conversion of ammonia to urea, and feed conversion ratio resulting in healthier and heavier animals. Methods of the invention can be used to improve animal health and agricultural productivity in the aforementioned ways and to reduce nitrate pollution in the environment.

Another advantage of the composition is in its ability to reduce a level of heavy metal contamination in an animal thereby improving the overall health of the animal.

Another advantage of the composition is to provide for the nutritional needs of dairy cows while minimizing weight loss or gain, preventing digestive problems, and maintaining good health and supporting high milk production. The management of the nutrition of dairy cows using the composition during the early lactation period advantageously affects milk yield throughout the entire lactation.

Another advantage of the composition is to include a significant quantity of undegradable protein to increase milk, egg, and meat productivity of livestock and poultry in comparison with traditional livestock feed rations and feeding practices.

Another advantage of the composition is to substantially prevent negative energy balance in ruminants.

Another advantage of the composition is to improve the conversion of ammonia to urea, which may reduce excessive amounts of ammonia in the body of a ruminant thereby improving ruminant liver function and overall health.

Another advantage of the composition is to prevent severe muscle contractions in ruminants, such as a downer cow, suffering from milk fever by providing the proper amount of calcium and magnesium in the animal's diet.

Another advantage of the methods described herein is the ability of the mastic gum processing method to avoid the use of pre-steaming or alcohol solvents to achieve tackiness. Unlike existing processing methods, the present method does not require alcohol for the product to remain soluble.

According to an embodiment of the present invention, a health improvement composition for improving the health of an animal in need of such improvement by assisting in the animal's metabolization of protein and facilitating the conversion of ammonia to urea is provided. The composition can include mastic gum, at least two ionic minerals including at least calcium and magnesium, and an amino acid. Ingestion of the composition by the animal improves the animal's feed conversion ratio by assisting the animal in metabolizing protein and converting harmful ammonia to less-harmful urea.

In another aspect of the invention, the animal can be a ruminant or a poultry bird.

In another aspect of the invention, the ruminant can be a bovine.

In another aspect of the invention, the composition can increase synthesis of milk in the ruminant.

In another aspect of the invention, the ionic minerals can be at least partially derived from an inland sea.

In another aspect of the invention, the calcium can be calcium in solution.

In another aspect of the invention, the calcium of the composition can be calcium carbonate that is milled to a particulate size.

In another aspect of the invention, the amino acid can be an essential amino acid not produced by the animal.

In another aspect of the invention, the composition can include a protein that includes the amino acid.

In another aspect of the invention, the composition can further include probiotics.

In another aspect of the invention, the at least one ionic mineral can be selected from among one or more of the following: magnesium, chloride, potassium, sulfate, sodium, boron, bromide, calcium, carbonate, silicon, nitrogen, selenium, phosphorus, iodine, chromium, iron, manganese, titanium, rubidium, cobalt, copper, antimony, molybdenum, strontium, zinc, nickel, tungsten, germanium, scandium, tin, lanthanum, yttrium, silver, gallium, zirconium, vanadium, beryllium, tellurium, bismuth, hafnium, terbium, europium, gadolinium, samarium, cerium, cesium, gold, dysprosium, holmium, lutetium, erbium, ytterbium, neodymium, praseodymium, niobium, tantalum, thorium, thallium, and rhenium.

The invention also relates to a composition for improving milk production by a ruminant in need of such improvement. The composition can include mastic gum, a source of calcium, a source of magnesium, at least one ionic mineral, and an essential amino acid that is not produced by the animal's own body.

In another aspect of the invention, the animal can be a ruminant or a poultry bird.

In another aspect of the invention, the at least one ionic mineral can be selected from among one or more of the following: magnesium, chloride, potassium, sulfate, sodium, boron, bromide, calcium, carbonate, silicon, nitrogen, selenium, phosphorus, iodine, chromium, iron, manganese, titanium, rubidium, cobalt, copper, antimony, molybdenum, strontium, zinc, nickel, tungsten, germanium, scandium, tin, lanthanum, yttrium, silver, gallium, zirconium, vanadium, beryllium, tellurium, bismuth, hafnium, terbium, europium, gadolinium, samarium, cerium, cesium, gold, dysprosium, holmium, lutetium, erbium, ytterbium, neodymium, praseodymium, niobium, tantalum, thorium, thallium, and rhenium.

The invention also relates to a method for improving a feed conversion ratio of an animal. The method can include the step of producing a composition for ingestion by an animal, wherein the composition can include: mastic gum, a source of calcium, a source of magnesium, and water comprising trace minerals dissolved therein. The method can further include the step of feeding the composition to the animal.

In another method of the invention, the composition can be added to a feed ration provided to the animal for ingestion.

In another method of the invention, the composition can be pelletized for ingestion by the animal.

In another method of the invention, the method further improves bone mineralization of the animal when the composition is ingested.

The invention also relates to a method for processing mastic gum. The method can include the steps of: (a) milling mastic gum tears into a powder; and (b) mixing the mastic gum powder with ionic minerals dissolved in water to dissolve the mastic gum so as to produce a solubilized mastic gum liquid solution.

In another method of the invention, the processing method produces a mastic gum liquid solution that is tacky.

In another method of the invention, the mastic gum liquid solution becomes tacky when mixed with feed for pelletizing a combination of the feed and composition and is useful as a binder for forming pellets.

In another method of the invention, the mastic gum liquid solution is soluble without requiring the use of isopropyl alcohol, methanol, another alcohol, acetone, hexane, chloroform, diethyl ether, n-butyl ether, or other chemical solvents.

The invention also relates to a method for reducing nitrate pollution in the environment. The method can include the step of producing a nitrate excretion-reducing composition for ingestion by an animal that includes mastic gum, a source of calcium, and water having trace minerals dissolved therein. The method also includes the step of feeding the composition to the animal.

The invention also relates to a method for improving milk production by a ruminant. The method can include the step of producing a composition for ingestion by an animal that includes mastic gum, a source of calcium, a source of magnesium, and water having trace minerals dissolved therein. The method can also include the step of feeding the composition to the animal.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

DETAILED DESCRIPTION

The present invention is best understood by reference to the detailed drawings and description set forth herein. Embodiments of the invention are discussed below with reference to the drawings; however, those skilled in the art will readily appreciate that the detailed description given herein with respect to these figures is for explanatory purposes as the invention extends beyond these limited embodiments. For example, in light of the teachings of the present invention, those skilled in the art will recognize a multiplicity of alternate and suitable approaches, depending upon the needs of the particular application, to implement the functionality of any given detail described herein beyond the particular implementation choices in the following embodiments described and shown. That is, numerous modifications and variations of the invention may exist that are too numerous to be listed but that all fit within the scope of the invention. In addition, singular words should be read as plural and vice versa and masculine as feminine and vice versa, where appropriate, and alternative embodiments do not necessarily imply that the two are mutually exclusive.

The present invention should not be limited to the particular methodology, compounds, materials, manufacturing techniques, uses, and applications, described herein, as these may vary. The terminology used herein is used for the purpose of describing particular embodiments only, and is not intended to limit the scope of the present invention. As used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" may be a reference to one or more steps or means and may include sub-steps and subservient means.

All conjunctions used herein are to be understood in the most inclusive sense possible. Thus, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. Structures described herein are to be understood also to refer to functional equivalents of such structures. Language that may be construed to express approximation should be so understood unless the context clearly dictates otherwise.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," "desirable," or "exemplary" and words of similar meaning should not be understood as implying that certain features are critical, essential, or even important to the structure or function of the invention, but instead as merely intended to highlight alternative or additional features that may or may not be utilized in a particular embodiment of the invention.

Those skilled in the art will also understand that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations; however, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C" is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

All numbers expressing dimensions, quantities of ingredients, reaction conditions, and so forth used in the specification are to be understood as being modified in all instances by the term "about" unless expressly stated otherwise. Accordingly, unless indicated to the contrary, the numerical parameters set forth herein are approximations that may vary depending upon the desired properties sought to be obtained.

An animal health improvement composition will now be discussed in greater detail. The animal may be a wild, domesticated, domestic, or livestock animal. The animal may also be a human. The animal health improvement composition may be discussed throughout this disclosure in the context of a ruminant in the interest of clearly illustrating an example of the present invention. A ruminant may include, but should not be limited to, a bovine. Throughout this disclosure, the ruminant may be referred to as a bovine, cow, cattle, or other type of ruminant in the interest of clearly illustrating various embodiments of the present invention. Any discussion relating to a species or group of species is not intended to limit the invention and that the many aspects of the present invention should apply to virtually all animals. Discussion herein concerning a ruminant, bovine, cow, or other species should not be construed to limit the scope of animals to which this invention may apply and with which the composition may be used.

The animal health improvement composition additionally may be discussed throughout this disclosure in the context of poultry in the interest of clearly illustrating an example of the present invention. Poultry may include, but should not be limited to, various domesticated birds such as a chicken, turkey, duck, goose, other fowl, or ostrich in the interest of clearly illustrating various embodiments of the present invention. However, any discussion relating to a species or group of species is not intended to limit the invention and that the many aspects of the present invention should apply to virtually all animals including wild birds. Discussion in the context of poultry and other birds should not be construed to limit the scope of animals to which this invention may apply and with which the composition may be used.

The composition affects a ruminant by about precisely meeting nutritional requirements for certain nutrients including trace minerals that are necessary for many metabolic processes but that are lacking in conventional feed and in the environment. The composition also lowers feed costs, increases reproductive performance of animals, increases milk protein yield, minimizes nitrogen excretion by assisting in the metabolization of protein to inhibit hyper-ammonia production by anaerobes in a rumen of a ruminant, and advances the onset of lactation in ruminants. The composition may also prevent negative energy balance in a ruminant. The composition may also improve conversion of ammonia to urea and reduce excessive ammonia in the body of a ruminant.

The composition affects poultry by about precisely meeting nutritional requirements for certain nutrients including trace minerals that are necessary for many metabolic processes but that are lacking in conventional feed and in the environment. The composition also lower feed costs, increases reproductive performance, increases egg yield and quality, and minimizes nitrogen excretion by assisting in the metabolization of protein. The composition may also prevent negative energy balance in poultry. The composition may also improve conversion of ammonia to urea and reduce excessive ammonia in the body of poultry.

The composition can include a mixture of ingredients including mastic gum, a source of calcium, and various trace minerals dissolved in water. The composition may also include a source of magnesium. Optionally, the composition can also include probiotics, the microorganisms of which can be selected based on the type of animal for which the composition is intended to correspond to and promote the growth of typical bioflora in the gut microbiome of such animal.

As previously mentioned, the composition can include a source of calcium that dissolves in water. In preferred embodiments, the source of calcium in solution is calcium carbonate. In other embodiments, other calcium-containing compounds that are safe for ingestion by animals may be included. The composition may contain only a single source or multiple sources of calcium. The calcium carbonate can be milled to between about 18 micrometers to about 44 micrometers before it is added to the composition although the particulate size of the milled calcium carbonate could be more or less than the specified range. The milled calcium carbonate can be added to water in which it ionizes into calcium and carbonate ions as it dissolves into liquid form. Once solubilized in water, the resulting liquid calcium becomes absorbable when ingested by the animal.

As also previously mentioned, the composition can contain a source of magnesium, which generally will be a magnesium salt or other magnesium-containing compound. Like the calcium, the magnesium may also be milled into a powder for dissolving in water to produce the composition.

The water of the composition can be distilled water or water obtained from body of water such as a lake, a spring, a river, or an ocean. In preferred embodiments of the composition, the water can be obtained from an inland body of saltwater (also referred to herein as an "inland sea") or from a mineral spring. Examples of suitable inland seas can include endorheic basins, which may include characteristics of high salinity and mineral content, or other sources of saltwater or mineral waters.

The mastic gum of the composition possesses anti-microbial properties and may provide many health benefits to an animal ingesting the composition. For example, mastic gum may improve the metabolization of protein, including catabolism of protein within the rumen of a ruminant by bacteria. Mastic gum also acts as a natural preservative and antibiotic. Mastic gum may also enhance the composition as an antioxidant reducing toxic free radicals in the animal's body and exhibits anti-inflammatory properties. Additionally, mastic gum supports good liver function and may inhibit *Staphylococcus aureus, Listeria monocytogenes, Klebsiella pneumoneae, Pseudomonas aeruginos, Salmonella typhi, Proteus mirabilis, Escherichia coli, Enterobacter cloacea, Candida albicans*, coccidiosis, and other infectious diseases.

Although trace minerals may no longer be as plentiful in feed rations, they may exist plentifully in their proper proportions in the mineral-rich waters of the earth's oceans and inland seas. The composition of the present invention includes formulations of ionic minerals that can be easily assimilated through the selectively permeable cell membranes of the animal's body.

In addition to the mineral content of the water in embodiments where the water is obtained from an inland body of saltwater, the composition can include calcium and magnesium added and dissolved in larger quantities than is found in the water. In some embodiments, the composition can also include additional potassium and sodium added and dissolved in larger quantities than is found in the water. The use of these minerals plus the ionic trace minerals found in the water in combination with the anti-inflammatory and anti-oxidant characteristics of mastic gum work to support muscle contractions and gastrointestinal tract health in animals. Excluding mastic gum and the additional minerals (i.e., additional calcium, magnesium, and possibly potassium and sodium) added to the composition, the ionic trace minerals dissolved in the water of the composition can be (shown in percentages by weight) about 69% chloride, about 28% magnesium, about 2% calcium, about 1% sodium, and less than about 1% potassium.

The composition may also include additional amounts of magnesium, chloride, potassium, sulfate, sodium, boron, bromide, calcium, carbonate, silicon, nitrogen, selenium, phosphorus, iodine, chromium, iron, manganese, titanium, rubidium, cobalt, copper, antimony, molybdenum, strontium, zinc, nickel, tungsten, germanium, scandium, tin, lanthanum, yttrium, silver, gallium, zirconium, vanadium, beryllium, tellurium, bismuth, hafnium, terbium, europium, gadolinium, samarium, cerium, cesium, gold, dysprosium, holmium, lutetium, erbium, ytterbium, neodymium, praseodymium, niobium, tantalum, thorium, thallium, and rhenium, plus other minerals typically found in seawater.

In one embodiment, the composition can include ionic trace minerals dissolved in water in about the following amounts shown in Table 1. Although the amounts shown in Table 1 pertain to a specific embodiment of the composition, the amounts of each mineral set forth below that is dissolved in the water of the composition could be more, less, or the same as the amounts indicated in Table 1. In some embodiments of the composition, certain minerals may be absent due to their lack of presence in a particular water source or may be omitted intentionally where minerals obtained from industrial sources are utilized to create the ionized mineral water. For example, harmful heavy metals, such as lead and mercury, can be excluded from the trace minerals included in the composition when trace minerals are obtained from industrial sources rather than as dissolved components of water obtained from natural sources.

TABLE 1

| | |
|---|---|
| Aluminum | 0.095 µg/ml |
| Antimony | 1.04 µg/ml |
| Arsenic | 0.38 ppm |
| Barium | 0.299 µg/ml |
| Beryllium | <0.02 µg/ml |
| Bismuth | 1.55 µg/ml |
| Boron | 0.556 mg/ml |
| Bromine | 2.29 µg/ml |
| Cadmium | <0.05 ppm |
| Calcium | 27.7 µg/ml |
| Carbon | 163 ppm |
| Cerium | 0.027 µg/ml |
| Cesium | 0.139 µg/ml |
| Chloride | 305.0 µg/ml |
| Chromium | 0.298 µg/ml |
| Cobalt | 0.059 µg/ml |
| Copper | 0.678 µg/ml |
| Dysprosium | <0.02 µg/ml |
| Erbium | <0.03 µg/ml |
| Europium | <0.03 µg/ml |
| Fluoride | 0.487 µg/ml |
| Gadolinium | 0.025 µg/ml |
| Gallium | 0.016 µg/ml |
| Germanium | <0.01 µg/ml |
| Gold | <0.01 µg/ml |
| Hafnium | <0.02 µg/ml |
| Holmium | <0.03 µg/ml |
| Indium | <0.01 µg/ml |
| Iodine | 1.19 µg/ml |
| Iridium | <0.05 µg/ml |
| Iron | 0.072 µg/ml |
| Lanthanum | 0.041 µg/ml |
| Lead | 0.023 ppm |
| Lithium | 0.754 µg/ml |
| Lutetium | <0.03 mg/ml |
| Magnesium | 109.2 mg/ml |
| Manganese | 0.233 µg/ml |
| Mercury | <0.01 ppm |
| Molybdenum | 0.358 µg/ml |
| Neodymium | 0.037 µg/ml |
| Nickel | 0.031 µg/ml |
| Niobium | 0.017 µg/ml |
| Osmium | <0.05 µg/ml |
| Palladium | <0.01 µg/ml |
| Phosphorus | 0.774 µg/ml |
| Platinum | <0.01 µg/ml |
| Potassium | 1.20 mg/ml |
| Praseodymium | 0.029 µg/ml |
| Rhenium | <0.02 µg/ml |
| Rhodium | <0.01 µg/ml |
| Rubidium | 0.665 µg/ml |
| Ruthenium | 0.013 µg/ml |
| Samarium | 0.018 µg/ml |
| Scandium | 0.045 µg/ml |
| Selenium | 0.767 µg/ml |

TABLE 1-continued

| | |
|---|---|
| Silicon | 1.55 µg/ml |
| Silver | 11.6 µg/ml |
| Sodium | 1.67 mg/ml |
| Strontium | 0.068 µg/ml |
| Sulfate | 21.70 mg/ml |
| Tantalum | 0.033 µg/ml |
| Tellurium | <0.03 µg/ml |
| Terbium | <0.02 µg/ml |
| Thallium | <0.03 µg/ml |
| Thorium | <0.05 µg/ml |
| Thulium | <0.01 µg/ml |
| Tin | 0.039 µg/ml |
| Titanium | 0.556 µg/ml |
| Tungsten | 0.75 µg/ml |
| Vanadium | 0.093 µg/ml |
| Ytterbium | <0.01 µg/ml |
| Yttrium | 0.021 µg/ml |
| Zinc | 0.517 µg/ml |
| Zirconium | 0.053 µg/ml |

As mentioned above, one or more of the ingredients may be found in or near one or more lake, for example, Utah's Great Salt Lake or the Dead Sea, which are rich in magnesium and other minerals.

The composition may also improve urea production in the animal's body, which has beneficial effects on milk production in ruminants and on general health in most animals. The urea may be produced by improved conversion of ammonia, advantageously reducing an amount of ammonia in the body of the animal. A part of the urea produced in the animal's body may be returned to the digestive tract in the saliva and by absorption through the rumen wall. The remainder of the urea may be passed off in the urine as waste.

Methods for Processing Mastic Gum

The invention further relates to a method for processing mastic gum, which may be used in any of the compositions described herein. The composition can be provided to ruminants, poultry, and other livestock animals, other non-farm animals, or to humans. The method produces a processed mastic gum that may advantageously remain tacky. The method of processing mastic gum does not use pre-steaming of the mastic gum and does not require the use of isopropyl alcohol, methanol, another alcohol, acetone, hexane, chloroform, diethyl ether, n-butyl ether, or other solvents to achieve tackiness or to dissolve the mastic gum. The processed mastic gum created by the method may remain tacky when applied to binders, such as feed and pellets. In one embodiment, the product may be a 4-to-1 extract.

The method may include collecting and using whole tears of mastic gum. The method of processing mastic gum can include optionally the step of separating tears of mastic gum into at least small and large groups based on tear diameter using a sieve or manual sorting. The method may also include an optional step of washing and drying the mastic gum tears.

In a next step, mastic gum tears can be mechanically milled into a powder. The mastic gum herb may be milled to a powder having a particulate size of between about 18 micrometers to about 42 micrometers. In preferred embodiments, the mastic gum is milled into powder having a particulate size of less than about 32 micrometers. In the most preferred embodiments, the mastic gum is milled into powder having a particulate size of less than about 18 micrometers.

The mastic gum powder is then mixed with ionic minerals dissolved in water. The water or the minerals can be sourced from an inland body of saltwater (e.g., the Great Salt Lake or the Dead Sea). Alternatively, minerals safe for consumption by animals can be purchased from industrial sources and added to water in predetermined amounts. The mixture can then be packaged and stored for later use.

The method produces processed mastic gum that is soluble without requiring the use of isopropyl alcohol, methanol, another alcohol, acetone, hexane, chloroform, diethyl ether, n-butyl ether, or other solvents.

Mastic gum used in the processing method may be Chios Gum Mastic (also known as Chios Mastiha), an air-dried resinous exudation from *P. Lentiscus* L. (Family Anacardiaceae), a small shrub-like evergreen tree. Mastic gum may support liver function, inhibit bacterial growth, and decrease a likelihood of contracting various bacterial and fungal infections including, for example, *Staphylococcus aureus, Listeria monocytogenes, Klebsiella pneumoneae, Pseudomonas aeruginos, Salmonella typhi, Proteus mirabilis, Escherichia coli, Enterobacter cloacea, Candida albicans*, and coccidiosis.

The ionically-charged minerals may include absorbable liquid calcium, magnesium, and ionically charged trace minerals derived from inland bodies of saltwater (e.g., Great Salt Lake or the Dead Sea). Inclusion of an ionically charged minerals helps the animal to completely absorb the minerals as the electrical charge attached to the mineral assists it in penetrating cellular barriers.

Method for Improving Feed Conversion Ratio

The invention also relates to a method for improving a feed conversion ratio of an animal. The method can include the steps of producing a composition for ingestion by an animal, and then feeding the composition to the animal. The composition can be any composition described herein. The feeding step of the method can be performed by adding one serving of the composition to a feed ration provided to the animal for ingestion. The feed ration can be any suitable feed normally provided for ingestion by an animal of the type to which the composition is being delivered. For an adult ruminant, one serving is about 16 fluid ounces (about 4.7 ml). For example, for ingestion by an adult ruminant, the composition may be added to the feed ration as a top dressing by pouring it onto the feed ration. In another embodiment, the composition can be premixed with the animal feed. Because the mastic gum remains tacky as a result of the processing method used to dissolve the mastic gum in water, the composition adheres easily to the feed ration so that an intended dose of the composition is ingested by the animal. The composition may also be pelletized for ingestion by the animal. In another embodiment, the composition can also be added to the water or other drink for imbibing by the animal.

For ingestion by a calf that is 3-6 months old, about 6 drops can be added to about 8-16 ounces of liquid or solid feed.

In an initial trial study of the efficacy of the method and composition, a number of steers were separated into eight control pens and eight test pens. The method was used with the eight test groups in which the steers in those test groups were administered the composition daily in addition to their typical feed according to the methods described above. The eight control groups were given only the typical feed and not the composition. Both the control and test groups experienced the same weight loss from weaning to the start of the study and both sets of groups experienced the same weight loss during the first 14 days after the study began. During the second 14-day period of the study (i.e., days 15-28), the test groups overall experienced a greater rebound in weight gain than the control groups. Five of the eight test groups experienced weight gains during the second 14-day period, while only three of the eight control groups experienced weight gains during that period. Preliminary analysis shows that the average weight of the cattle in the test groups was also significantly more (481 pounds) on day 28 of the study than the average weight of the cattle in the control groups on the same day (462 pounds).

Method for Reducing Nitrate Pollution

The invention also relates to a method for reducing nitrate pollution in the environment. The method can include the steps of producing a composition for ingestion by an animal, and then feeding the composition to the animal. The composition can be any composition described herein. Once ingested, the composition assists the animal in better metabolizing proteins and facilitates the conversion of toxic ammonia in the animal's body to less harmful urea that can be either excreted by the animal or reabsorbed.

Method for Improving Milk Production

The invention also relates to a method for improving milk production by a ruminant. The method can include the steps of producing a composition for ingestion by an animal, and then feeding the composition to the animal. The composition can be any composition described herein. In tests of the method and composition performed on 800 dairy cows, the level of milk urea nitrogen (MUN) was increased from about 12-17 mg/dl (considered a healthy MUN level) from an original level for these animals of about 6-7 mg/dl. Maintaining a healthy MUN level is advantageous because elevated MUN levels result from cattle being fed too much rumen degradable protein or too much rumen undegradable protein and in either case is both expensive in feed cost and causes reduced reproductive performance.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A health improvement composition for improving the health of an animal in need of such improvement by assisting in the animal's metabolization of protein and facilitating conversion of ammonia to urea, the composition consisting of:
  alcohol-free mastic gum powder milled to have a particulate size of between 18 micrometers and 42 micrometers; wherein mastic gum used to produce the alcohol-free mastic gum powder is produced using water only and no other solvents; and
  two added ionic minerals consisting of 2% calcium by weight and 28% magnesium by weight;
  wherein ingestion of the composition by the animal improves the animal's feed conversion ratio by assisting the animal in metabolizing protein and converting harmful ammonia to less-harmful urea;
  wherein the animal is a bovine, a poultry bird, or a ruminant.

2. A method for improving a feed conversion ratio of an animal, the method comprising the steps of:
  (a) producing a composition for ingestion by an animal, the composition consisting of:
    (i) water comprising trace minerals;
    (ii) alcohol-free mastic gum powder milled to have a particulate size of between 18 micrometers and 42 micrometers; wherein mastic gum used to produce the alcohol-free mastic gum powder is produced using water only and no other solvents; and (iii) two added ionic minerals consisting of 2% calcium by weight and 28% magnesium by weight; and (b) feeding the composition to the animal to improve the feed conversion ratio of the animal.

3. A pH-reducing health improvement composition for improving the health of an animal in need of such improvement by increasing acidity in a gut of the animal to assist in the animal's metabolization of protein and to facilitate conversion of ammonia to urea, the composition consisting of:

alcohol-free mastic gum powder milled to have a particulate size of between 18 micrometers and 42 micrometers; wherein mastic gum used to produce the alcohol-free mastic gum powder is produced using water only and no other solvents;

two added ionic minerals consisting of 2% calcium by weight and 28% magnesium by weight; and one or more other added ionic minerals;

wherein ingestion of the composition by the animal increases acidity in the animal's gut to improve the animal's feed conversion ratio by assisting the animal in metabolizing protein and converting high-pH ammonia to lower-pH urea;

wherein the animal is a bovine, a poultry bird, or a ruminant.

4. A health improvement composition for improving the health of an animal in need of such improvement by assisting in the animal's metabolization of protein and facilitating conversion of ammonia to urea, the composition consisting of:

alcohol-free mastic gum powder milled to have a particulate size of between 18 micrometers and 42 micrometers; wherein mastic gum used to produce the alcohol-free mastic gum powder is produced using water only and no other solvents;

two added ionic minerals consisting of 2% calcium by weight and 28% magnesium by weight; and one or more other added ionic minerals;

wherein ingestion of the composition by the animal improves the animal's feed conversion ratio by assisting the animal in metabolizing protein and converting harmful ammonia to less-harmful urea;

wherein the animal is a chicken.

* * * * *